(12) United States Patent
Stanley et al.

(10) Patent No.: US 9,943,298 B2
(45) Date of Patent: Apr. 17, 2018

(54) VASCULAR CLOSURE WITH SHAPE MEMORY CHARACTERISTIC

(71) Applicant: Cook Medical Technologies LLC, Bloomington, IN (US)

(72) Inventors: Cleon Stanley, Bloomington, IN (US); Ram H. Paul, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 751 days.

(21) Appl. No.: 14/056,470

(22) Filed: Oct. 17, 2013

(65) Prior Publication Data

US 2014/0114348 A1    Apr. 24, 2014

Related U.S. Application Data

(60) Provisional application No. 61/716,182, filed on Oct. 19, 2012.

(51) Int. Cl.
*A61B 17/00* (2006.01)

(52) U.S. Cl.
CPC ............. *A61B 17/0057* (2013.01); *A61B 2017/00628* (2013.01)

(58) Field of Classification Search
CPC ...... A61B 2017/00628; A61B 17/0057; A61B 2017/00659
See application file for complete search history.

(56) References Cited

U.S. PATENT DOCUMENTS

| | | |
|---|---|---|
| 4,744,364 A | 5/1988 | Kensey |
| 5,085,629 A | 2/1992 | Goldberg et al. |
| 5,269,809 A | 12/1993 | Hayhurst et al. |
| 5,312,435 A | 5/1994 | Nash et al. |
| 5,342,393 A | 8/1994 | Stack |
| 5,350,399 A | 9/1994 | Erlebacher et al. |
| 5,411,520 A | 5/1995 | Nash et al. |
| 5,531,759 A | 7/1996 | Kensey et al. |
| 5,545,178 A | 8/1996 | Kensey et al. |
| 5,620,461 A | 4/1997 | Muijs Van De Moer |
| 5,662,681 A | 9/1997 | Nash et al. |
| 5,700,277 A | 12/1997 | Nash et al. |
| 5,800,436 A | 9/1998 | Lerch |

(Continued)

FOREIGN PATENT DOCUMENTS

| | | |
|---|---|---|
| EP | 0 534 696 A1 | 3/1993 |
| EP | 1 169 968 A1 | 1/2002 |

(Continued)

OTHER PUBLICATIONS

International Search Report and Written Opinion issued in PCT/US2012/066173, dated Mar. 8, 2013.

(Continued)

*Primary Examiner* — Corrine McDermott
*Assistant Examiner* — Tin Nguyen
(74) *Attorney, Agent, or Firm* — Woodard, Emhardt, Moriarty, McNett & Henry LLP

(57) ABSTRACT

Among other things, there is disclosed devices for closing an internal opening, e.g. a hole in a blood vessel, that includes a shape memory function. Particular substances have been found to provide advantages in use, and in particular forms of closure structures.

18 Claims, 4 Drawing Sheets

(56) References Cited

U.S. PATENT DOCUMENTS

| | | |
|---|---|---|
| 5,916,236 A | 6/1999 | van de Moer |
| 5,964,744 A | 10/1999 | Balbierz et al. |
| 6,071,301 A | 6/2000 | Cragg et al. |
| 6,190,400 B1 | 2/2001 | Van De Moer et al. |
| 6,281,262 B1 | 8/2001 | Shikinami |
| 6,425,911 B1 | 7/2002 | Akerfeldt |
| 6,491,714 B1 | 12/2002 | Bennett |
| 6,508,828 B1 | 1/2003 | Akerfeldt et al. |
| 6,596,013 B2 | 7/2003 | Yang et al. |
| 6,726,696 B1 * | 4/2004 | Houser .............. A61B 17/0057 606/151 |
| 6,755,868 B2 | 6/2004 | Rousseau |
| 6,764,500 B1 | 7/2004 | Muijs Van De Moer et al. |
| 6,860,895 B1 | 3/2005 | Akerfeldt et al. |
| 6,921,401 B2 | 7/2005 | Lerch et al. |
| 6,939,363 B2 | 9/2005 | Akerfeldt |
| 7,048,710 B1 | 5/2006 | Cragg et al. |
| 7,169,168 B2 | 1/2007 | Muijs Van De Moer et al. |
| 7,338,514 B2 | 3/2008 | Wahr et al. |
| 7,524,914 B2 | 4/2009 | Mather et al. |
| 7,597,705 B2 | 10/2009 | Forsberg et al. |
| 7,621,937 B2 | 11/2009 | Pipenhagen et al. |
| 7,658,748 B2 | 2/2010 | Marino et al. |
| 7,717,929 B2 | 5/2010 | Fallman |
| 7,875,052 B2 | 1/2011 | Kawaura et al. |
| 7,931,671 B2 | 4/2011 | Paul et al. |
| 7,985,415 B2 | 7/2011 | Giroux |
| 7,993,367 B2 | 8/2011 | Bagaoisan et al. |
| 8,034,046 B2 | 10/2011 | Eidenschink |
| 8,105,352 B2 | 1/2012 | Egnelov |
| 8,124,705 B2 | 2/2012 | Hasson et al. |
| 8,257,389 B2 | 9/2012 | Chanduszko et al. |
| 8,480,709 B2 | 7/2013 | Chanduszko et al. |
| 8,652,166 B2 | 2/2014 | Akerfeldt |
| 2003/0181988 A1 | 9/2003 | Rousseau |
| 2005/0085855 A1 | 4/2005 | Forsberg |
| 2005/0169974 A1 | 8/2005 | Tenerz |
| 2005/0283187 A1 | 12/2005 | Longson |
| 2006/0142797 A1 | 6/2006 | Egnelov |
| 2006/0206146 A1 | 9/2006 | Tenerz |
| 2007/0123936 A1 | 5/2007 | Goldin et al. |
| 2007/0198059 A1 | 8/2007 | Patel et al. |
| 2008/0071310 A1 | 3/2008 | Hoffman et al. |
| 2008/0114395 A1 | 5/2008 | Mathisen et al. |
| 2008/0208265 A1 * | 8/2008 | Frazier ............... A61B 17/0401 606/326 |
| 2008/0287986 A1 | 11/2008 | Thor et al. |
| 2008/0312684 A1 | 12/2008 | Drasler et al. |
| 2009/0018574 A1 | 1/2009 | Martin |
| 2009/0054926 A1 | 2/2009 | Pipenhagen et al. |
| 2009/0088793 A1 | 4/2009 | Bagaoisan et al. |
| 2009/0112257 A1 | 4/2009 | Preinitz |
| 2009/0143817 A1 | 6/2009 | Akerfeldt |
| 2009/0216267 A1 | 8/2009 | Willard et al. |
| 2009/0234377 A1 | 9/2009 | Mahlin |
| 2010/0042144 A1 | 2/2010 | Bennett |
| 2010/0087854 A1 | 4/2010 | Stopek et al. |
| 2010/0217308 A1 | 8/2010 | Hansen et al. |
| 2010/0217309 A1 | 8/2010 | Hansen et al. |
| 2011/0066181 A1 | 3/2011 | Jenson et al. |
| 2011/0288581 A1 | 11/2011 | Paul et al. |
| 2012/0116447 A1 | 5/2012 | Stanley et al. |

FOREIGN PATENT DOCUMENTS

| | | |
|---|---|---|
| EP | 1 266 626 A1 | 12/2002 |
| EP | 1 413 255 A1 | 4/2004 |
| EP | 1 440 661 | 7/2004 |
| EP | 2 064 999 A2 | 6/2009 |
| WO | 1999/33402 | 7/1999 |
| WO | WO 2000/078226 | 12/2000 |
| WO | WO 2005/063133 A1 | 7/2005 |
| WO | WO 2006/075228 | 7/2006 |
| WO | WO 2007/059243 A1 | 5/2007 |
| WO | WO 2011/146729 A2 | 11/2011 |

OTHER PUBLICATIONS

International Search Report and Written Opinion issued in PCT/US2011/037173, dated Nov. 17, 2011.

* cited by examiner

VASCULAR CLOSURE WITH SHAPE MEMORY CHARACTERISTIC

This application claims the benefit of U.S. Provisional Application Ser. No. 61/716,182 (filed on Oct. 19, 2012), which is incorporated herein by reference in its entirety.

The present disclosure concerns devices and systems for closing openings in vascular walls, such as those made in blood vessels during catheterization procedures. In particular, it concerns devices and systems with internal anchoring or sealing members that exhibit shape memory characteristics.

BACKGROUND

A number of devices and techniques for closing a hole in the side of a wall of a blood vessel made for intravascular access or other purposes have been proposed. Foams, plugs, caps and other structures have been developed for application over or within such holes, to limit or eliminate blood loss through such holes. In the realm of internal caps, seals or toggles, such a piece must be inserted through the hole, then retracted in an orientation such that the cap, seal or toggle will engage the vascular wall at points to the side of the hole. Insertion usually occurs through a cannula or other tube extending through the hole, and naturally in order to be inserted through the tube and hole such an internal piece must be smaller than the tube and hole during insertion.

Several difficulties with using such systems exist. For example, a compressed plug or cap forced into a delivery tube may be constrained by the tube, and therefore have a significant amount of force or friction between the tube and the plug or cap. Moving the plug or cap out of the tube is accordingly difficult. If a plug or cap is constrained in a compressed condition by something other than the tube, it may be easier to move the plug or cap out of the tube. However, once out of the tube, the plug or cap may not be oriented as desired, or may not properly extend or expand following insertion, e.g. the constraint holding the item in a compressed state is not overcome. If the plug or cap does not open sufficiently, it can be pulled back through the hole rather than engaging against the vessel wall. Similarly, thin or very flexible plugs or caps may not have sufficient sturdiness to hold when pulled against the vascular wall, resulting in unwanted eversion or pulling back through the hole.

Accordingly, there is needed an internal seal or anchoring member that is not only bioabsorbable and will securely anchor a closure and/or seal a hole in a vascular wall, but that will also regularly open or expand in an expected way when placed in the blood vessel. Such an item would address the problems noted above, and perhaps others.

SUMMARY

Among other things, there is disclosed a vascular closure device that includes an internal member for placement within a blood vessel in the blood flow therein. The internal member is of a material comprising polycaprolactone and L-lactide in exemplary embodiments, and in particular between approximately 27 to 38 percent polycaprolactone and between approximately 62 and 73 percent L-lactide in block copolymer form. The internal member has a first unfolded or open configuration and a second folded or closed configuration, and is adapted to hold the second configuration without external force applied to it at a temperature less than body temperature. The internal member is adapted to adjust toward the first configuration when heat is applied to the internal member in the second configuration sufficient to increase its temperature to about 37 degrees Celsius, e.g. when inserted into the blood stream of a patient. The internal member exhibits shape-memory characteristics.

Specific embodiments of the material for the internal member include between approximately 30 to 35 percent polycaprolactone and between approximately 65 to 70 percent L-lactide in block copolymer form by themselves or with other substances, such as substances that do not significantly affect the shape-memory characteristics. The material may include polycaprolactone and L-lactide in a ratio of between approximately 3:7 and 7:13 with respect to each other. Examples of the first unfolded or open configuration include the internal member being at least partially in the shape of a dome, and/or having two opposing rim portions each forming part of a circle or ellipse, and two parallel side surfaces intersecting each of the rim portions. Examples of the internal member can include a monolithic stem extending proximally. Preferably, the device is adapted to be placed in the body via a placement apparatus having a lumen with an internal diameter, and when the internal member is in the second configuration a dimension of the member measured in a direction perpendicular to the stem is less than the internal diameter of the lumen of the placement apparatus. When the internal member is in the first configuration, the dimension of the member may be greater than the internal diameter of the lumen of the placement apparatus.

Embodiments of a vascular closure system are disclosed that include a delivery tube having a longitudinal lumen with a first diameter and a closure device including an internal member for anchoring the closure device from within a blood vessel, wherein the internal member has a first unstressed, normal or expanded condition and a second stressed or compact condition. In the first condition, the internal member has a width dimension greater than the first diameter, and in the second condition the width dimension of the internal member is reduced so that the width dimension is smaller than the first diameter. The second condition is held by the internal member without external application of force. When the internal member in the second condition is moved from within the tube into a blood vessel in which blood is flowing at body temperature, the internal member moves from the second condition toward the first condition without substantial absorption of fluid.

In particular examples, at least the internal member includes a material comprising between approximately 27 to 38 percent polycaprolactone and between approximately 62 and 73 percent L-lactide in block copolymer form, such as between approximately 30 to 35 percent polycaprolactone and between approximately 65 and 70 percent L-lactide. The material may be solely or essentially polycaprolactone and L-lactide, so that specific embodiments may be approximately 30 percent polycaprolactone and approximately 70 percent L-lactide, or approximately 35 percent polycaprolactone and approximately 65 percent L-lactide. These or other examples of materials can include polycaprolactone and L-lactide in a ratio between approximately 3:7 and 7:13 between them, and can be in block copolymer form. The internal member in the first condition may be at least partially dome-shaped, and/or may include two rim portions that are substantially in the shape of at least part of an ellipse, and first and second side edges that are parallel to each other and on either side of a center point, the first and second side edges each intersecting the two rim portions.

DESCRIPTION OF THE ILLUSTRATED EMBODIMENTS

Figure 1:
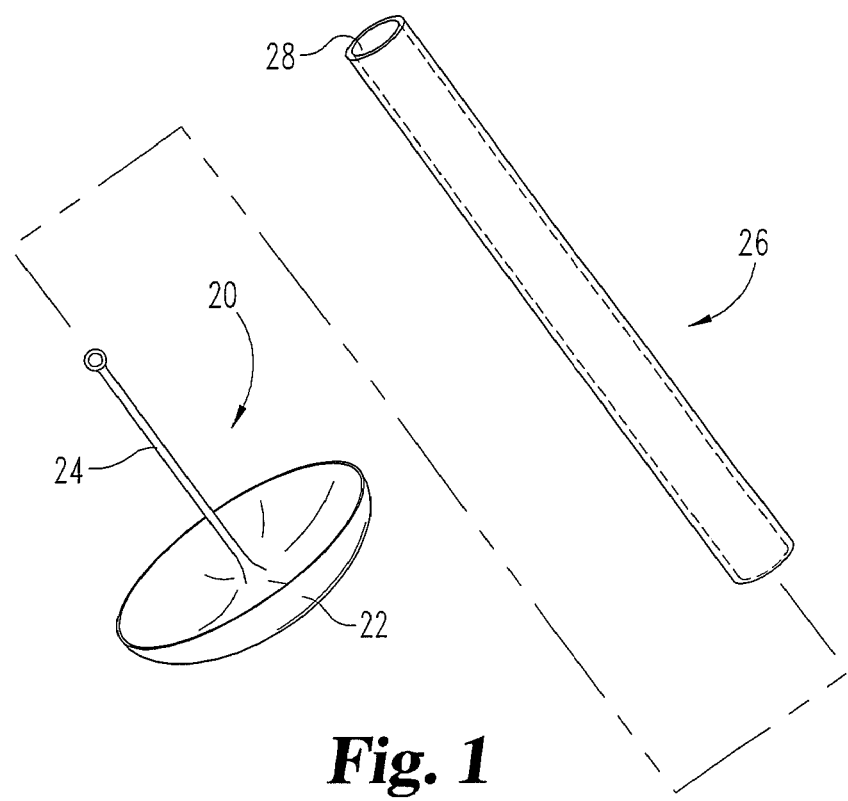
FIG. 1 is an exploded perspective view of an embodiment of a closure device and system (not necessarily to scale) according to the present disclosure.

For the purposes of promoting an understanding of the principles of the disclosure, reference will now be made to certain embodiments and specific language will be used to describe the same. It will nevertheless be understood that no limitation of the scope of this disclosure and the claims is thereby intended, such alterations, further modifications and further applications of the principles described herein being contemplated as would normally occur to one skilled in the art to which this disclosure relates. In several figures, where there are the same or similar elements, those elements are designated with the same or similar reference numerals.

Referring now generally to the drawings, there is shown an embodiment of a device for closing a bodily opening, in the particular form of a vascular closure device 20. Closure 20 in the illustrated embodiment includes an inner anchoring or sealing member 22, with an elongated member 24 extending from inner member 22. A delivery device 26 is also described for insertion of closure 20. Generally, inner member 22 is inserted through a lumen 28 of delivery device 26 that extends through a hole in a vessel, so that member 22 is inside device 26 and elongated member 24 extends proximally through and/or out of device 26. Examples of such devices and structures (including exemplary sealing or anchoring members) are found in U.S. patent application Ser. No. 13/111,338 (filed on May 19, 2011); Ser. No. 13/303,707 (filed on Nov. 23, 2011); 61/716,155 (filed on Oct. 12, 2012) and 61/716,182 (filed on Oct. 12, 2012), all of which are incorporated herein by reference in their entireties.

Figure 2A:
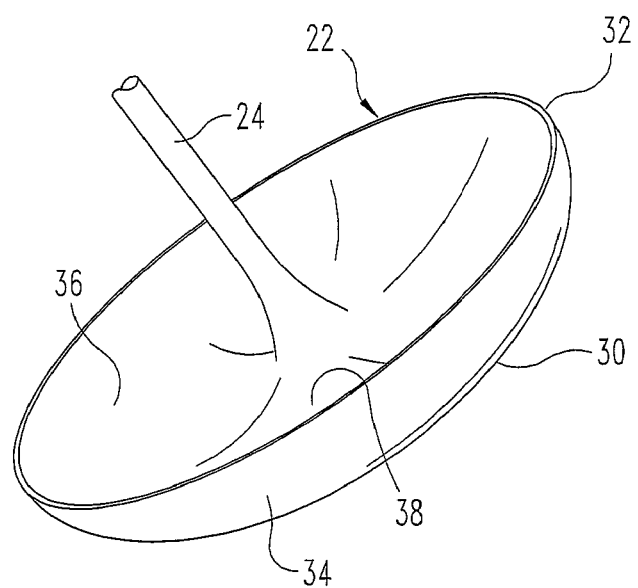
FIG. 2A is a perspective view of a portion of the device of FIG. 1.
Figure 2B:
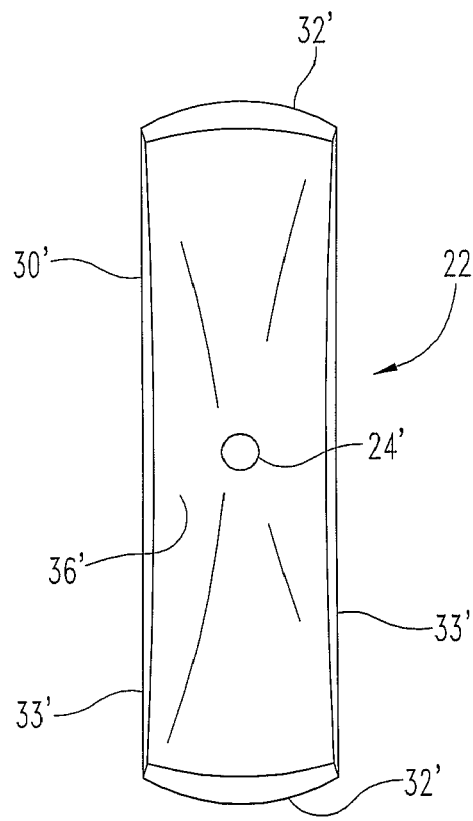
FIG. 2B is a top plan view of another embodiment of a closure device.

Examples of inner member 22 in two particular embodiments are shown in FIGS. 2A and 2B. The embodiment of inner member 22 shown in FIG. 2A is a substantially dome-shaped element, having a wall 30 defining a rim 32, an exterior convex surface 34 and an interior concave surface 36. Wall 30 can have a constant or varying thickness, for example in certain embodiments having a maximum thickness in the range of about 0.0050 inches to about 0.050 inches, and in a particular embodiment about 0.015 inches. In the illustrated embodiment, the maximum thickness of member 22 is at and/or between the connection(s) with elongated member 24, and the thickness decreases uniformly out to rim 32. Inner member 22 is part-spherical or part-spheroidal in an open, natural or unstressed state (e.g. FIG. 2A), having a substantially circular or oval-shaped (e.g. elliptical) rim 32. Rim 32 is substantially in one plane in this embodiment, having little breadth. Exterior convex surface 34 and interior concave surface 36 are continuous in the illustrated embodiment, and surface 36 is open and unobstructed in an initial expanded configuration. In particular embodiments, surfaces 34 and 36 may have substantially the same radii, so that the overall thickness of wall 30 is substantially constant, or may have differing radii, so that they intersect or approach each other at (and wall 30 thins toward) rim 32. A center point 38, where elongated member 24 meets inner member 22 in this embodiment, may have a tangent plane at exterior surface 34 that is substantially parallel to the plane of rim 32.

Figure 2C:
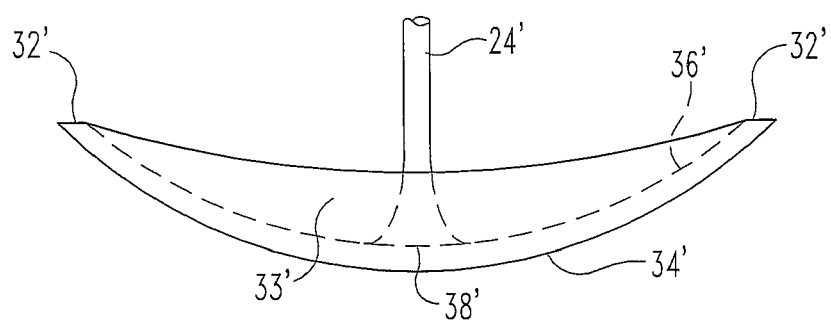
FIG. 2C is a side view of the embodiment of FIG. 2B.

An alternative toggle form of inner member 22' is shown in FIGS. 2B and 2C in the form of a curved segment or portion of a dome. In that embodiment, wall 30' defines a rim 32', an exterior convex surface 34' and an interior concave surface 36'. Wall 30' can have a thickness as described above with respect to the embodiment of wall 30. In the illustrated embodiment, the maximum thickness of member 22' is at and/or between the connection(s) with elongated member 24', and the thickness decreases uniformly out to rim 32'. Inner member 22' is part-spherical or part-spheroidal in an open, natural or unstressed state (e.g. FIGS. 2B, 2C), having a rim 32' forming part of a substantially circular or oval shape (e.g. an ellipse). The illustrated embodiment of member 22' includes side surfaces 33' that are generally linear or planar and offset from the center of member 22'. In other embodiments side surfaces 33' may be slightly convex, having a different radius of curvature than rim 32'. Rim 32' is substantially in one plane in this embodiment, having little or no breadth. Member 22' has an exterior convex surface 34' and an interior concave surface 36' which is open and unobstructed. In particular embodiments, surfaces 34' and 36' may have substantially the same radii, so that the overall thickness of wall 32' is substantially constant, or may have differing radii, so that they intersect or approach each other at (and wall 30' thins toward) rim 32'. A center point 38' may have a tangent plane that is parallel to the plane of rim 32'.

Member 22 can be constructed so as to completely flatten (e.g. surface 36 substantially conforming to surrounding tissue) under stress as experienced after implantation, or so as to not completely flatten under such stress (e.g. maintaining an at least slightly concave surface 26 or arch) in use, as discussed further below. Member 22 in particular embodiments is made of a material that is biocompatible and naturally degrades in and/or is absorbed by the body (e.g. material(s) that are broken down, dissolved and/or otherwise disintegrated by the body or its fluids so that they do not leave foreign material or require further procedures, as by hydrolysis, enzymatic degradation, or other processes).

A class of material that the inventors have found to be particularly useful in creating a dome-shaped inner member 22, 22' is polycaprolactone/L-lactide blends. These materials include sturdiness and biodegradability that is desirable in vascular closure systems. It has further been discovered that particular ratios of polycaprolactone to L-lactide have particular advantages in that they provide advantageous shape-memory properties in the context of vascular closures (e.g. insertion into a blood environment). Compounds comprising between about 30% polycaprolactone to about 70% L-lactide and about 15% polycaprolactone to about 85% L-lactide have been tested and shown to provide shape-memory properties, holding a stressed form or configuration at a lower temperature and resuming an unstressed form or configuration in a warmer environment. In particular embodiments, the compounds disclosed herein provide members 22 that show not only an ability to maintain a stressed form or configuration until warmed, but also have compliance or softness qualities that allow for some bending and elasticity. Thus, in the stressed form or configuration (e.g. folded as indicated below) at a lower temperature, member 22 can be bent or flexed as opposed to rigid materials, and will return to the stressed form or configuration. As noted, it is a warmer environment that changes the member 22 back to and unstressed form or configuration. The blends have been used in both their amorphous and crystalline (block copolymer) forms.

In particular, it has been determined that a blend of between about 27% and 38% polycaprolactone with the remainder being L-lactide (i.e. about 73% to about 62% L-lactide) in block copolymer form will provide advantageous shape-memory characteristics that overcome existing problems, and provide advantages in preparing and using vascular closures. Particular blends of about 35% polycaprolactone with about 65% L-lactide and of about 30% polycaprolactone with about 70% L-lactide have each been tested by the inventors and found to exhibit the useful properties noted below. Accordingly, it is believed that a blend of at least 27% polycaprolactone with the remainder being L-lactide is beneficial for the purposes noted herein.

In testing prototype anchoring members, the inventors unexpectedly observed shape memory characteristics in the anchoring members substantially as shown in FIG. 2B. The blends noted above were used in preparing and testing anchoring members. Examples of such anchoring members were folded substantially in half toward a stem (e.g. a shape akin to a taco shell in round or elliptical embodiments of the anchoring member, indicated in FIG. 3A). The anchoring members made with the blends noted above retained that folded shape provided by the stress of folding. They were loaded into a delivery tube, and maintained that folded shape within the tube. They demonstrated the advantage of being easily slid along delivery tube, since the anchoring members did not expand within the tube so that the tube exerted a constraining force (with resultant friction during insertion) on them. The anchoring members maintained the folded or compact condition until immersed into warming fluid. When deployed during testing into a fluid having a temperature of about 36 degrees Celsius to about 44 degrees Celsius, e.g. approximately the normal temperature of blood within a patient, the anchoring members prepared as noted above evenly opened from its folded "taco" shape and returned to a molded dome shape.

It is believed that the anchoring members return to the set molded shape (e.g. FIGS. 2A-2C, 3B) as a result of the particular polycaprolactone/L-lactide blends noted above. For example, testing demonstrated that the best exhibition of the characteristics of holding form in a folded or other stressed configuration and expanding when warmed was found in the above-described blends of those substances. The stresses placed on the blended material during molding and/or folding are believed to contribute to the holding characteristic. Injection molding of the polycaprolactone/L-lactide blends noted above, in the small molds needed for internal sealing or anchoring members as described herein, results in highly-oriented polymer molecules. Cooling following the molding also helps set the polymer in a desired form. The members allow bending or folding at about room temperature or lower to be held. The application of heat to the folded members 22, 22' with their molecular orientation is believed to be the factor that allows them to change from the compact or folded state to the expanded initial state. The polycaprolactone does not permit significant absorption of water into item 22, 22', and so absorption does not appear to cause a resumption of an initial shape, and item 22, 22' is not swelled or otherwise altered in thickness or weight in the insertion and shape-change process.

One advantage of such a behavior in the anchoring member is that it makes placement easier and reduces or eliminates likelihood of the anchoring member pulling out through a vascular hole during placement. Thinness or flexible characteristics of a sealing closure can result in the member not maintaining a folded condition inside a delivery tube, but expanding within it to press against, and be restrained by, the interior surface of the tube. Such expansion within the tube creates friction or forced engagement of the anchoring member with the tube, and such force or engagement must be overcome when moving the anchoring member out of the tube. There can also be a risk that a folded internal anchoring or sealing member will not open as desired in the vessel. When the internal member is retracted so that it contacts a portion of the vessel, if it is not expanded substantially from its folded condition, its profile can allow it to slip through or widen the vascular hole. In such cases, it is necessary to insert a new closure, and may result in loss of blood or other complications.

By using inner members as disclosed herein, with material (such as that described previously) that is resorbable and exhibits shape-memory characteristics by maintaining a stressed or compact configuration substantially below body temperature and returning to an initial expanded (unstressed) configuration when warmed to or toward body temperature, an anchoring member using such material begins expansion when placed in the warming blood stream. The ability to remain folded and reduce friction or contact with the inside of the delivery tube is combined with reliable expansion to a desired initial configuration (e.g. a sturdy dome-like shape) on insertion into the warm bodily environment. The chance that the anchoring member remains folded when retracted against the vascular wall is reduced or eliminated, resulting in greater chance of success and less likelihood of complications for the closure procedure.

The elongated member 24, 24' in the embodiments of FIGS. 2A-2C are stems, i.e. one particular stem for or as a part of each elongated member connected to anchoring or sealing member 22. Stem 24 extends from the concave interior of member 22, in particular embodiments joining member 22 at or near center point 38. In certain embodiments, stem 24 is of the same material as member 22, and is molded with member 22 as a unitary or monolithic piece. Stem 24 permits connection to a filament (not shown) that extends proximally and guides a locking member, buffer material, or other pieces for use with system or device 20. In other embodiments, an elongated 24 may be a flexible suture or other filament engaged to member 22, with properties akin to a stem to allow holding of member 22 against the vessel.

An example of the use of member 22 in closing a hole in a blood vessel wall is discussed below. It will be understood that similar or identical devices can be used in treating other tissues, afflictions, wounds or the like.

Figure 3A:
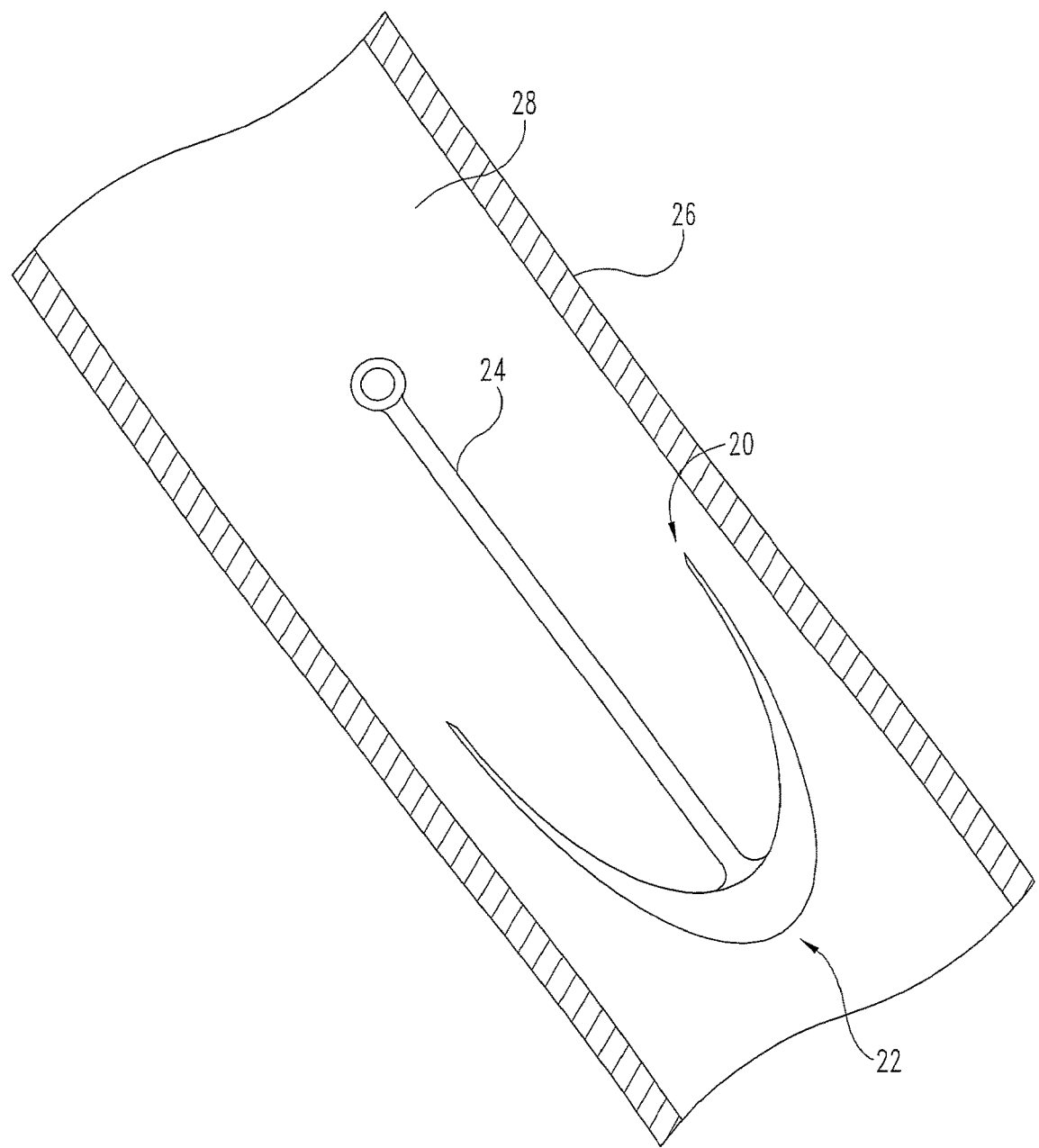
FIG. 3A is a part cross-sectional view of an embodiment as in FIG. 1 with a closure device embodiment in a compact configuration.
Figure 3B:
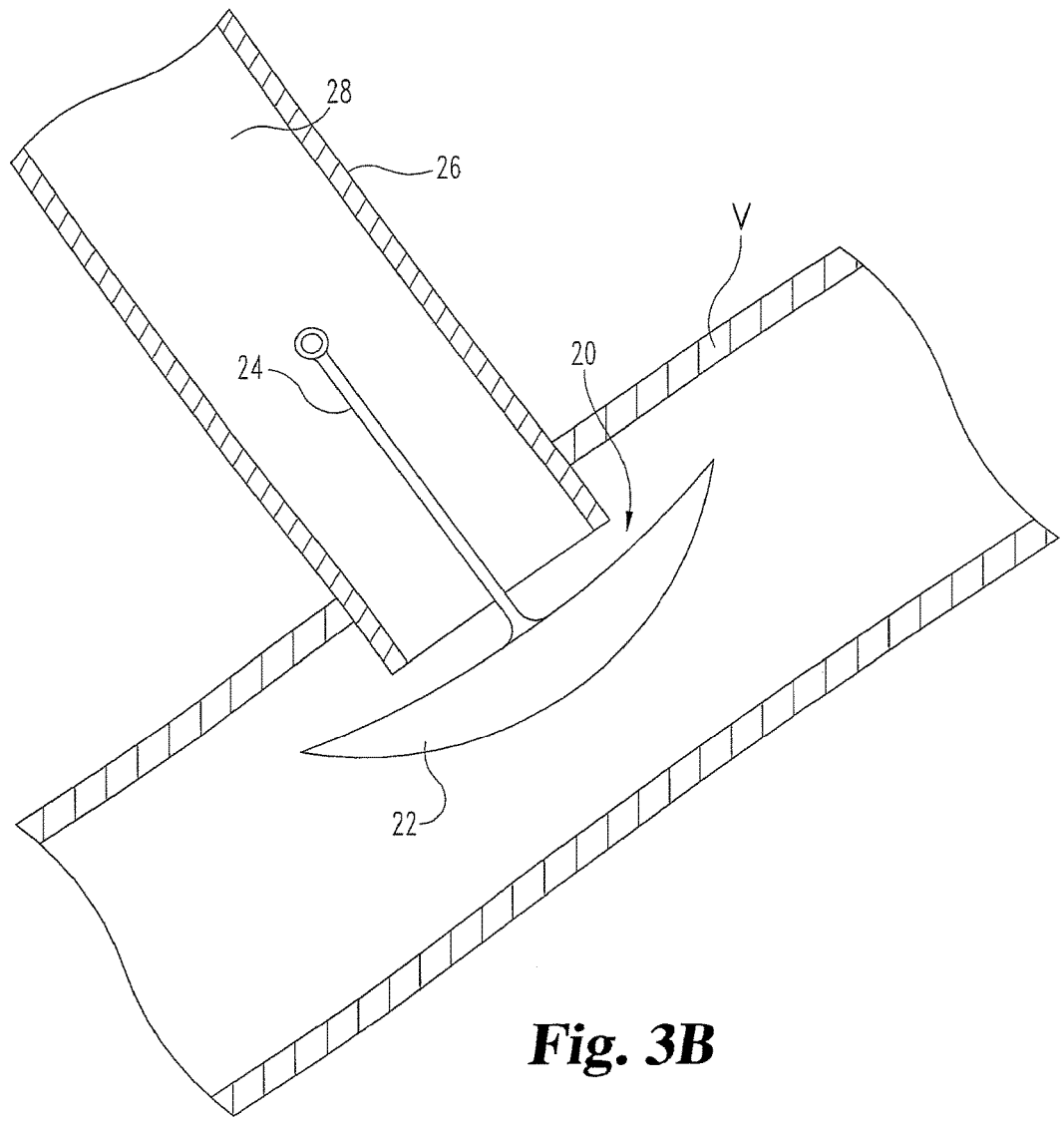
FIG. 3B is a part cross-sectional view of the embodiment in FIG. 3A with a closure device embodiment in an expanded configuration.

As indicated in FIG. 3A, anchoring or sealing member 22 is folded or compacted and is placed in the lumen 28 of delivery device 26. Within device 26, member 22 maintains its compact configuration. While it may touch device 26 during normal use, member 22 does not expand within device 26 to press against its internal diameter, i.e. the wall surrounding lumen 28. When device 26 is placed through a hole to be closed in a vessel wall V (FIG. 3B), member 22 is moved out of device 26 so that member 22 is within the flow of blood within the vessel. The rise in temperature in member 22 generated by the blood flow results in member

What is claimed is:

1. A vascular closure device, comprising
an internal member for placement within a blood vessel in the blood flow therein, the internal member being a curved segment of a dome having first and second rim portions, an exterior convex surface and an interior concave surface, and first and second planar side surfaces between the rim portions and offset from a center of the internal member,
wherein the internal member is of a material comprising between approximately 27 to 38 percent polycaprolactone and between approximately 62 and 73 percent L-lactide in block copolymer form, wherein the internal member has a first unfolded or open configuration and a second folded or closed configuration, the internal member adapted to hold the second configuration without external force applied to it at a temperature less than body temperature, and wherein the internal member is adapted to adjust toward the first configuration when heat is applied to the internal member in the second configuration sufficient to increase its temperature to about 37 degrees Celsius.

2. The device of claim 1, wherein the material comprises between approximately 30 to 35 percent polycaprolactone and between approximately 65 to 70 percent L-lactide in block copolymer form.

3. The device of claim 1, wherein the material consists essentially of approximately 30 to 35 percent polycaprolactone and between approximately 65 to 70 percent L-lactide in block copolymer form.

4. The device of claim 1, wherein in the first unfolded or open configuration, the rim portions each form part of a circle or ellipse having respective concave curvatures around a line through the center point, and the first and second planar side surfaces intersect each of the rim portions.

5. The device of claim 1, wherein the material comprises polycaprolactone and L-lactide in a ratio of between approximately 3:7 and 7:13.

6. The device of claim 1, wherein the internal member includes a monolithic stem extending proximally.

7. The device of claim 6, wherein the device is adapted to be placed via a placement apparatus having a lumen with an internal diameter, and wherein in the second configuration a dimension of the internal member measured in a direction perpendicular to the stem is less than the internal diameter of the lumen of the placement apparatus.

8. The device of claim 7, wherein in the first configuration the dimension of the internal member is greater than the internal diameter of the lumen of the placement apparatus.

9. The device of claim 1, wherein the first and second planar side surfaces have a concave curvature and intersecting each of the rim portions, wherein the concave curvature of the first and second planar side surfaces has a smaller radius of curvature than the interior concave surface.

10. A vascular closure system, comprising:
a delivery tube having a longitudinal lumen bounded by a wall with a first inner diameter;
a closure device including an internal member for anchoring the closure device from within a blood vessel, wherein the internal member has an internal concave surface, a first unstressed expanded condition and a second compact condition,
wherein at least the internal member comprises a material comprising polycaprolactone and L-lactide in a ratio between approximately 3:7 and 7:13,
in the first condition the internal member has a width dimension greater than the first inner diameter,
in the second condition the internal member is folded so that the width dimension is smaller than the first inner diameter, the second folded condition being held by the internal member without external application of force, wherein the internal member in the second folded condition does not expand within the delivery tube to press against the wall of the delivery tube and is movable longitudinally through the lumen and into a vessel,
and wherein when the internal member in the second condition is moved from within the delivery tube into a blood vessel in which blood is flowing at body temperature, the internal member moves from the second condition toward the first condition without substantial absorption of fluid.

11. The system of claim 10, wherein the material comprises between approximately 27 to 38 percent polycaprolactone and between approximately 62 and 73 percent L-lactide in block copolymer form.

12. The system of claim 11, wherein the material comprises between approximately 30 to 35 percent polycaprolactone and between approximately 65 and 70 percent L-lactide in block copolymer form.

13. The system of claim 12, wherein the internal member consists essentially of polycaprolactone and L-lactide.

14. The system of claim 12, wherein the internal member consists of polycaprolactone and L-lactide.

15. The system of claim 10, wherein at least the internal member consists essentially of approximately 30 percent polycaprolactone and approximately 70 percent L-lactide.

16. The system of claim 10, wherein the internal member in the first condition is at least partially dome-shaped.

17. The system of claim 16, wherein the internal member includes two rim portions that are substantially in the shape of at least part of an ellipse and having respective concave curvatures, and first and second side edges that are parallel to each other and on either side of a center point, the first and second side edges each intersecting the two rim portions and the curvatures are around a line through the center point.

18. The system of claim 10, wherein the material is in block copolymer form.

* * * * *